United States Patent [19]

Cassady et al.

[11] Patent Number: 5,763,632
[45] Date of Patent: Jun. 9, 1998

[54] PROCESS FOR MAKING ISETHIONATE ESTER SALTS

[75] Inventors: Timothy John Cassady, Hamilton; Norman Milstein, Montgomery, both of Ohio; Richard P. Crews, Simpsonville, S.C.

[73] Assignee: Henkel Corporation, Plymouth Meeting, Pa.

[21] Appl. No.: 598,159

[22] Filed: Feb. 7, 1996

Related U.S. Application Data

[63] Continuation of Ser. No. 144,266, Oct. 28, 1993, abandoned.

[51] Int. Cl.⁶ .................................................. C07C 303/00
[52] U.S. Cl. .................................. 554/92; 554/96; 554/97
[58] Field of Search ............................ 554/92, 96, 97

[56] References Cited

U.S. PATENT DOCUMENTS

| | | | |
|---|---|---|---|
| 2,597,696 | 5/1952 | Anthes et al. | 260/513 |
| 2,810,747 | 10/1957 | Sexton et al. | 260/513 |
| 2,820,818 | 1/1958 | Sextar | 260/573 |
| 2,894,912 | 7/1959 | Geitz | 252/121 |
| 3,004,049 | 10/1961 | Schenck et al. | 554/92 |
| 3,094,555 | 6/1963 | Lamberti et al. | 260/513 |
| 3,151,136 | 9/1964 | Koczorowski et al. | 260/400 |
| 3,376,229 | 4/1968 | Haass et al. | 252/117 |
| 4,003,925 | 1/1977 | Lamberti et al. | 260/513 R |
| 4,180,470 | 12/1979 | Tokosh et al. | 252/121 |
| 4,206,069 | 6/1980 | Borrello | 252/122 |
| 4,405,526 | 9/1983 | Lamberti et al. | 260/400 |
| 4,476,055 | 10/1984 | Du Vernet | 260/400 |
| 4,515,721 | 5/1985 | Login et al. | 260/400 |
| 4,536,338 | 8/1985 | Urban et al. | 260/400 |
| 4,663,070 | 5/1987 | Dobrovoiny et al. | 252/121 |
| 4,695,395 | 9/1987 | Caswell et al. | 252/121 |
| 4,851,147 | 7/1989 | Esposito et al. | 252/108 |
| 4,954,281 | 9/1990 | Resch | 252/107 |
| 4,954,282 | 9/1990 | Rys | 252/117 |
| 4,963,284 | 10/1990 | Novakonic et al. | 252/108 |
| 5,030,376 | 7/1991 | Lee et al. | 252/108 |
| 5,041,233 | 8/1991 | Kutny et al. | 252/121 |
| 5,132,037 | 7/1992 | Greene et al. | 252/108 |
| 5,185,101 | 2/1993 | Weipert | 252/554 |

FOREIGN PATENT DOCUMENTS

| | | |
|---|---|---|
| 0459769 | 12/1991 | European Pat. Off. . |
| 0813593 | 8/1960 | United Kingdom . |
| 1059984 | 2/1967 | United Kingdom . |

OTHER PUBLICATIONS

CA 51: 16514e (1957).
Nature 160, 795–6 (1947).

Primary Examiner—Paul J. Killos
Assistant Examiner—Deborah D. Carr
Attorney, Agent, or Firm—Wayne C. Jaeschke; John E. Drach; Daniel S. Ortiz

[57] ABSTRACT

Fatty acid esters of isethionate salts are made by reacting ethylene oxide and a bisulfite salt in an aqueous solution while maintaining the pH in the range of from about 5.5 to about 6.5 and while maintaining the temperature in the range of from 25° C. to 85° C. to form an isethionate salt. The isethionate salt is then esterified with a fatty acid to produce a product having little or no unwanted fatty acid esters of ethylene glycol.

9 Claims, No Drawings

PROCESS FOR MAKING ISETHIONATE ESTER SALTS

This application is a continuation of application Ser. No. 08/144,266, filed on Oct. 28, 1993, now abandoned.

BACKGROUND OF THE INVENTION

1. Field of the Invention

This invention relates to a process for making fatty acid esters of isethionic acid which minimizes the formation of unwanted by-products.

2. Description of the Related Art

Sodium and ammonium salts of the fatty acid esters of isethionic acid, 2-hydroxyethanesulfonic acid, are useful as mild, foaming surfactants in personal skin cleansing products. These isethionate ester salts are usually manufactured by first forming an isethionate salt by reaction of ethylene oxide with an aqueous solution of a bisulfite salt such as sodium bisulfite or ammonium bisulfite. The free alcohol functionality of the isethionate salt is then esterified with a fatty acid to produce a fatty acid ester of the isethionate salt. One of the principal problems encountered in this process is the production of ethylene glycol during the reaction of ethylene oxide and the bisulfite salt. The ethylene glycol thus formed subsequently reacts with the fatty acid in the second step of the process resulting in the formation of mono- and diesters of ethylene glycol which are only partially soluble in aqueous-based formulations of the product wherein the solids content is greater than 30% by weight. These partially soluble materials result in the formation of a hazy, aqueous product that contains fine solids which are difficult and costly to remove.

It would be advantageous to avoid the formation of the ethylene glycol fatty acid esters so that a clear aqueous product can be obtained without the need for additional processing steps which add to the cost of the product. The present invention is a method for making fatty acid esters of ammonium isethionate which minimizes the formation of ethylene glycol which in turn lowers the chance that fatty acid esters of ethylene glycol will form and contaminate the final product.

SUMMARY OF THE INVENTION

It has been discovered surprisingly that a fatty acid ester of an isethionate salt wherein the amount of mono- and di-fatty acid esters of ethylene glycol are held to a minimum can be made by a two step process. In the first step, ethylene oxide and a bisulfite salt are reacted in an aqueous solution while the pH of the solution is maintained in the range of from 5.5 to 6.5 and the temperature of the solution is maintained in the range of from 25° C. to 85° C. The control of the pH and the temperature in this first step of the process minimizes the formation of ethylene glycol while maximizing the amount of the desired product which is an isethionate salt. The amount of ethylene glycol formed is less than 0.85% based on the weight of a 60% aqueous solution of the isethionate salt. A fatty acid ester of the isethionate salt is then formed in the second step by reaction of the isethionate salt with a fatty acid. Because the amount of ethylene glycol formed is equal to or less than 0.85% by weight of the isethionate salt, the amount of mono- and di-fatty acid esters of ethylene glycol formed in the competing esterification of ethylene glycol by the fatty acid is low enough so that a clear aqueous product at ambient temperature is obtained.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

In the process according to the invention, ethylene oxide and a bisulfite salt are reacted in aqueous solution to form an isethionate salt which is a salt of 2-hydroxyethanesulfonic acid. The bisulfite salt can be introduced into the reaction as the salt itself such as by adding sodium bisulfite or it may be made in situ such as by the reaction of aqueous ammonia (ammonium hydroxide) and sulfur dioxide. In a preferred embodiment of the process according to the invention, ammonium bisulfite is reacted with ethylene oxide. Ammonium bisulfite can be made by any method known to those skilled in the art. Most preferably, the ammonium bisulfite is made in situ by reaction of aqueous ammonia (ammonium hydroxide) and sulfur dioxide. In general, the ethylene oxide is added to the aqueous solution of ammonia incrementally and alternately with the sulfur dioxide at such a rate that the reaction temperature is maintained in the range of from 25° C. to 85° C. and the pH is maintained in the range of from 5.5 to 6.5. Control of the reaction temperature in the 25° C. to 85° C. range and the pH in the 5.5 to 6.5 are essential features of the process according to the invention. The amount of ethylene glycol formed in the process according to the invention is a function of the combination of the reaction temperature and the pH. When the reaction temperature is maintained in the 25° C. to 85° C. range and the pH is maintained in the 5.5 to 6.5 range, the maximum amount of ethylene glycol formed is 0.85% based on the weight of a 60% aqueous solution of the isethionate salt. When the reaction temperature is maintained in the 60° C. to 65° C. range and the pH is maintained in the 5.8 to 6.2 range, the maximum amount of ethylene glycol formed is 0.50% based on the weight of a 60% aqueous solution of the isethionate salt. It is preferred to maintain the reaction temperature in the 60° C. to 65° C. range and the pH in the 5.8 to 6.2 range in order that the ethylene glycol concentration be kept below 0.50% based on the weight of a 60% aqueous solution of the isethionate salt.

The pH can be controlled by addition of aqueous base, preferably aqueous ammonia to the reaction mixture. The reaction temperature can be controlled by adjusting the addition rate of ethylene oxide and/or sulfur dioxide or by cooling the reaction mixture by any heat exchange means known to those skilled in the art or by a combination of an adjustment of the ethylene oxide/sulfur dioxide addition rates and by using a heat exchange means.

While any saturated or unsaturated carboxylic acid can be used in the process according to the invention, carboxylic acids traditionally classified as fatty acids, those having from 6 to 22 carbon atoms, are preferred. Fatty acids having from 8 to 18 carbon atoms are most preferred. The fatty acid can be a mixture of fatty acids such as those obtained from naturally occurring fats and oils. A preferred mixture of fatty acids is a coconut oil fatty acid composition comprised of (weight %) 6% $C_{10}$, 49–51% $C_{12}$, 18–19% $C_{14}$, 9–10% $C_{16}$, 7% $C_{18:0}$, 1–3% $C_{18:1}$ fatty acids.

When the process according to the invention is used to manufacture ammonium cocoyl isethionate, a composition comprising: (a) ammonium cocoyl isethionate; (b) ammonium isethionate; (c) coconut fatty acid; (d) triethanolamine; and (e) water is realized which provides a synthetic detergent solution useful for the manufacture of personal care products such as shampoo, liquid hand soap, shower gel, personal cleansing bars, and the like.

The following examples are meant to illustrate but not to limit the invention.

EXAMPLE 1

Preparation of Ammonium Isethionate

A reactor was charged with 29 parts of water and evacuated to a pressure of 50–75 mm Hg. The reactor was repressurized with nitrogen to a pressure of 20 psig and the reevacuated to a pressure of 50–75 mm Hg. About 25.5 parts of 28% aqueous ammonium hydroxide were then added and the reactor was pressurized to 6 psig with nitrogen. The first of a series of sulfur dioxide-ethylene oxide addition cycles was commenced by adding a portion of the required 26.7 parts of sulfur dioxide at a rate such that the reaction temperature was maintained in the 60°–70° C. range and in such an amount that the pH reached a value of 5.7–5.8. If, during the sulfur dioxide addition, the pH dropped below 5.7. it was adjusted back to 5.7 by addition of 28% aqueous ammonium hydroxide. After the sulfur dioxide addition was complete, the reaction mixture was stirred for 10 minutes at 60°–70° C. The reactor was then purged to 30 psig with nitrogen and vented back to 6 psig whereupon a portion of 18.5 parts of ethylene oxide were added while the temperature was maintained at 60°–65° C. and until the pH rose to 6.2. The total pressure over the reaction was never allowed to exceed 50 psig. After reaching a pH of 6.2 by the addition of a portion of the ethylene oxide, successive sulfur dioxide-ethylene oxide addition cycles were carried out during each of which the reaction temperature was maintained in the 60°–65° C. range and the pH was maintained in the 5.8–6.2 until all of the sulfur dioxide and ethylene oxide were added. The pH was maintained in the 5.8–6.2 range if necessary, by the addition of 28% aqueous ammonium hydroxide. The alternate additions of sulfur dioxide and ethylene oxide are continued until the sum of the ammonium sulfite and ammonium bisulfite equals 0.25 to 0.05% as measured by iodometric titration (iodine-thiosulfate). After these levels are reached, an amount of 35% hydrogen peroxide sufficient to convert the remaining ammonium sulfite and ammonium bisulfite to ammonium sulfate and ammonium bisulfate is added. The effect of reaction temperature and pH on the ethylene glycol content of ammonium isethionate is shown in Table 1 which is a listing of data from 14 reactions carried out according to the method set forth in this Example 1. The data show that when the pH of the reaction solution is maintained in the range of from 5.5 to 6.5 and the temperature of the solution is maintained in the range of from 25° C. to 85° C. the amount of ethylene glycol formed is less than 0.85% based on the weight of a 60% aqueous solution of the isethionate salt.

EXAMPLE 2

Preparation of Ammonium Cocoyl Isethionate (ACI)

A reactor was charged with 329 lbs. of coconut fatty acid (6% $C_{10}$, 49–51% $C_{12}$, 18–19% $C_{14}$, 9–10% $C_{16}$, 7% $C_{18:0}$, 1—3% $C_{18:1}$ fatty acids), 370 lbs. of the ammonium isethionate solution from Example 1 (59% aqueous solution), 251 grams (0.55 lbs.) of 99% methanesulfonic acid and 258 grams (0.55 lbs.) of 50% hypophosporous acid. The pressure was reduced to 25 inches of vacuum and the reactor was heated to 130° C.–150° C. Water, which began to distill over at 70°–80° C., was continuously removed until the theoretical amount of water from the ammonium isethionate solution, 151 lbs., was collected. The vacuum was then decreased to 15 inches and the temperature was increased to 175±5° C. The mixture was held at 175±5° C. and 15 inches of vacuum for 4 hours. The vacuum was increased to 25 inches and the temperature was then increased to 190° C. After the temperature reached 190° C., the mixture was held at 190° C. and 25 inches of vacuum for 3 hours. The reaction mixture was sampled and the conversion to ammonium cocoyl isethionate was assessed by Epton titration (Nature 160, 795–6 (1947); Trans. Faraday Soc., 44, 226–30 (1948), the entire contents of which are incorporated herein by reference) and $^1$H NMR analysis (see Example 3). The reaction mixture was maintained at 190° C. and 25 inches of vacuum until the Epton titration indicated sufficient conversion to ammonium cocoyl isethionate (this is indicated by Epton titration values of from 81–89%) at which time 12.3 lbs. of triethanolamine in 992 lbs. of water were rapidly added to lower the temperature to 50° C. The pH was adjusted to 6.6–6.8 with further additions of triethanolamine and the solids content was adjusted to 30–33% by adding water.

EXAMPLE 3

$^1$ H NMR Method for Composition of ACI

About 0.03 g of reaction mixture was dissolved in $d_6$-DMSO containing 0.5% (v/v) TMS and diluted to a volume of 1 ml. The $^1$H NMR spectrum was recorded using a Varian Unity 400 NMR spectrometer operating at 400 MHz. The integration of the triplet at $\delta$ 2.77 for the $CH_2$ group adjacent to the sulfonate group was used to indicate the relative molar amount of ACI. The integration of the triplet at $\delta$ 2.67 for the $CH_2$ group adjacent to the sulfonate group was used to indicate the relative molar amount of ammonium isethionate (AI). The integration of the triplet at $\delta$ 2.18 for the $CH_2$ group adjacent to the carboxyl group was used to indicate the relative molar amount of fatty acid (RCOOH). The relative molar amounts are used to calculate a molar ratio of ACI to AI to fatty acid and then to calculate percentages by weight of these molecules in the product according to the following method. The mole ratio of ACI, AI, and RCOOH is calculated by dividing the integration area for each of the peaks at $\delta$ 2.77, $\delta$ 2.67, and $\delta$ 2.18 by the total of the integration areas for these three peaks. The % conversion of AI is then found by dividing the mole % of ACI by the sum of the mole % of AI and ACI.

TABLE 1

| # | pH | Temp[1] | % EG[2] | Reactant[3] | EO/SO$_2$[4] |
|---|------|---------|---------|-----------|-------|
| 1 | 5.0–6.5 | 83–87 | 1.2 | NH$_4$SO$_3$H | — |
| 2 | 5.0–6.6 | 83–87 | 1.3 | NH$_4$SO$_3$H | — |
| 3 | 5.6–6.2 | 84 | 0.82 | NH$_4$OH | 1.016 |
| 4 | 5.3–6.5 | 84–85 | 1.36 | NH$_4$OH | — |
| 5 | 5.3–6.2 | 84–85 | 0.93 | NH$_4$OH | 1.00 |
| 6 | 5.8–6.2 | 83–84 | 0.62 | NH$_4$OH | 1.02 |
| 7 | 5.8–6.1 | 83–84 | 0.65 | NH$_4$OH | 1.00 |
| 8 | 5.8–6.1 | 83–85 | 0.66 | NH$_4$OH | 1.00 |
| 9 | 5.9–6.2 | 83–85 | 0.64 | NH$_4$OH | — |
| 10 | 5.9–6.2 | 66 | 0.46 | NH$_4$OH | 1.00 |
| 11 | 5.8–6.1 | 61–62 | 0.40 | NH$_4$OH | 1.00 |
| 12 | 5.8–6.2 | 65–66 | 0.43 | NH$_4$OH | 1.00 |
| 13 | 5.8–6.2 | 75–76 | 0.56 | NH$_4$OH | 1.02 |
| 14 | 5.8–6.2 | 70 | 0.52 | NH$_4$OH | 1.01 |

[1]- ethylene oxide addition temperature (°C.)
[2]- Wt. % ethylene glycol formed
[3]- NH$_4$SO$_3$H -added as ammonium bisulfite and then reacted with ethylene oxide
NH$_4$OH - ammonium bisulfite made in situ by reaction of NH$_4$OH + SO$_2$
[4]- mole ratio of EO/SO$_2$ when NH$_4$SO$_3$H made in situ

What is claimed is:

1. A process for making a composition comprising a fatty accid ester of ammonium isethionate, which forms a clear solution in water at a concentration of 30% by weight, comprising the steps of: (1) reacting ammonia, sulfur dioxide and ethylene oxide in an aqueous solution while maintaining the pH in the range of from 5.5 to 6.5 and maintaining the temperature in a range of from 25° C. to about 85° C. to form an ammonium isethionate salt solution, which at 60% by weight of ammonium isethionate contains not more than 0.85% by weight of ethylene glycol; (2) reacting said ammonium isethionate with a fatty acid to form the fatty acid ester of ammonium isethionate.

2. The process of claim 1 wherein said fatty acid is a composition comprised of, on a weight percent basis, 6% $C_{10}$, 49–51% $C_{12}$, 18–19% $C_{14}$, 9–10% $C_{16}$, 7% $C_{18:0}$, 1–3% $C_{18:1}$ fatty acids.

3. The process of claim 1 wherein step (2) is carried out in the presence of a catalyst comprised of methanesulfonic acid and hypophosporous acid.

4. The process of claim 1 wherein said pH range of step (1) is from about 5.8 to about 6.2 and said temperature range is from 60° C. to 65° C.

5. A process for making a composition comprising a fatty acid ester of ammonium isethionate, which forms a clear solution in water at a concentration of 30% by weight, comprising the steps of: (1) reacting ethylene oxide and ammonium bisulfite in an aqueous solution while maintaining the pH in the range of from about 5.5 to about 6.5 and maintaining the temperature in the range of 25° C. to 85° C. to form an ammonium isethionate solution which at 60% by weight of ammonium isethionate contains not more than 0.85% by weight of ethylene glycol; (2) reacting said ammonium isethionate with a fatty acid to form the fatty acid ester of ammonium isethionate.

6. The process of claim 5 wherein said fatty acid is a composition comprised of, on a weight percent basis, 6% $C_{10}$, 49–51% $C_{12}$, 18–19% $C_{14}$, 9–10% $C_{16}$, 7% $C_{18:1}$, 1–3% $C_{18:1}$, fatty acids.

7. The process of claim 5 wherein step (2) is carried out in the presence of a catalyst comprised of methanesulfonic acid and hypophosporous acid.

8. The process of claim 5 wherein said pH range of step (1) is from about 5.8 to about 6.2 and said temperature range of from 60° C. to 65° C.

9. A process for making a composition comprising ammonium cocoyl isethionate, which forms a clear solution at a concentration of 30% by weight, which comprises the steps of: (1) adding sulfur dioxide and ethylene oxide to ammonia in an aqueous solution at a rate sufficient to maintain the temperature of said solution in the range of from about 60° C. to about 65° C. while maintaining the pH of said solution in the range of from 5.5 to 6.5 to form an ammonium isethionate solution which at 60% by weight of ammonium isethionate contains not more than 0.85% by weight ethylene glycol; (2) reacting said ammonium isethionate with coconut oil fatty acids in the presence of a catalyst comprised of methanesulfonic acid and hypophosphorous acid to form the ammonium cocoyl isethionate.

* * * * *